(12) United States Patent
Oren et al.

(10) Patent No.: US 11,839,636 B1
(45) Date of Patent: Dec. 12, 2023

(54) PHARMACEUTICAL COMPOSITION BASED ON PLANT RAW MATERIALS: #2.1

(71) Applicants: Babry Oren, Van Nuys, CA (US); Sasha Moshe, Alpharetta, GA (US)

(72) Inventors: Babry Oren, Van Nuys, CA (US); Sasha Moshe, Alpharetta, GA (US)

( * ) Notice: Subject to any disclaimer, the term of this patent is extended or adjusted under 35 U.S.C. 154(b) by 0 days.

(21) Appl. No.: 17/815,548

(22) Filed: Jul. 27, 2022

(51) Int. Cl.
| | |
|---|---|
| *A61K 36/15* | (2006.01) |
| *A61K 36/87* | (2006.01) |
| *A61K 36/906* | (2006.01) |
| *A61K 9/00* | (2006.01) |
| *A61K 36/31* | (2006.01) |
| *A61K 36/67* | (2006.01) |
| *A61K 36/82* | (2006.01) |

(52) U.S. Cl.
CPC ............ *A61K 36/15* (2013.01); *A61K 9/0056* (2013.01); *A61K 36/31* (2013.01); *A61K 36/67* (2013.01); *A61K 36/82* (2013.01); *A61K 36/87* (2013.01); *A61K 36/906* (2013.01)

(58) Field of Classification Search
CPC ...... A61K 36/87; A61K 36/906; A61K 36/82; A61K 36/31; A61K 6/185; A61K 36/67; A61K 9/48; A61K 36/9068; A61K 36/15
See application file for complete search history.

(56) References Cited

U.S. PATENT DOCUMENTS

| | | | | |
|---|---|---|---|---|
| 9,861,670 | B2 * | 1/2018 | Clements | A61K 45/06 |
| 11,083,764 | B1 * | 8/2021 | Oren | A61K 36/87 |
| 11,458,181 | B2 * | 10/2022 | Chao Lee | A61K 36/884 |
| 11,517,604 | B2 * | 12/2022 | Ko | A61P 29/00 |
| 11,528,929 | B2 * | 12/2022 | Beller | A23L 33/30 |

FOREIGN PATENT DOCUMENTS

| | | | | |
|---|---|---|---|---|
| CN | 112996525 A | * | 6/2021 | ............ A61K 36/28 |
| TR | 201517712 A | * | 6/2016 | |

* cited by examiner

*Primary Examiner* — Aaron J Kosar

(57) ABSTRACT

A pharmaceutical composition containing dry powder of pine (*Pinus*) needles and dry peels and pits of grapes extract and pharmaceutically acceptable additive, dry extracts of ginger (*Zingiber officinale*), green tea (*Camellia sinensis*), yellow ginger (*Curcuma longa*), yellow mustard (*Brassica hirta*) seeds, white pepper, pomegranate (*Punica granatum*) bark and dry powder of pomegranate (*Punica granatum*) juice.

4 Claims, No Drawings

PHARMACEUTICAL COMPOSITION BASED ON PLANT RAW MATERIALS: #2.1

TECHNICAL FIELD

The invention relates to the pharmaceutical industry and applies to pharmaceutical compositions made on plant raw materials, which can be used as antidepressant, immunomodulatory, antiviral, antibacterial, antioxidant agents, as well as for the removal of heavy metals, free radicals (1) and radionuclides from the body.

BACKGROUND ART

Depression is characterized by emotional suppression, slowing down thinking, and limitation of speech and actions. Depression significantly interferes with the normal life and work of individuals.

Nowadays, antidepressants are widely used to treat depression. Mainly they are tricyclic antidepressants and monoamine oxidase inhibitors. These medicines have many, significantly expressed side effects.

It is well known to use a tincture of valerian roots to treat mild depressive conditions, although this drug is less effective and it is practically ineffective in cases of moderate and severe cases of depression.

A pharmaceutical composition based on plant raw materials (U.S. Ser. No. 11/083,764 (Babry Oren) 10.08.2021), which contains dry powder of pine needles and dry peels and pits of grapes extract and pharmaceutically acceptable additive, dry extracts of ginger, green tea, yellow ginger, yellow mustard seeds, white pepper, pomegranate bark and dry powder of pomegranate juice is also known. This composition is administered orally[V1] (2) and represents a strong immunomodulatory, antiviral, antibacterial, antioxidant agent to remove heavy metals and radionuclides from the body. However, it should be mentioned that this composition practically lacks antidepressant effect.

The development of herbal remedies that have expressed antidepressant activity, fewer side effects, a wide range of therapeutic properties, including immunomodulatory, antiviral, antibacterial, antioxidant activity, as well as the ability to remove heavy metals, free radicals (3) and radionuclides from the body is still relevant.

BRIEF DISCLOSURE OF THE INVENTION

One object of the invention is the pharmaceutical composition based on plant raw materials, which contains dry powder of pine (*Pinus*) needles and dry peels and pits of grapes extract and pharmaceutically acceptable additive, dry extracts of *Rhodiola Rosea* (*Rhodiola Rosea*), peony (*Paeonia*), green tea (*Camellia sinensis*), Ginkgo Biloba (*Ginkgo Biloba*), valerian (*Valeriána officinális*) roots, combination of dry powder of pomegranate (Punica granatum) juice and dry extract of pomegranate (Punica granatum) bark and folic acid, in the following ratio of the components in weight % (w %):

| | |
|---|---|
| dry powder of pine needles and dry peels and pits of grapes extract and pharmaceutically acceptable additive | 12-52 |
| dry extract of Rhodiola Rosea | 15-52 |
| dry extract of peony | 18-49 |
| dry extract of green tea | 1.2-5 |
| dry extract of Ginkgo Biloba | 4.5-19 |
| dry extract of valerian roots | 2-14 |
| combination of dry powder of pomegranate juice and dry extract of pomegranate bark | 0.5-7.6 |
| folic acid | 0.1-2 |

In the preferable version of the invention embodiment, the combination of dry powder of pomegranate juice and dry extract of pomegranate bark contains equal amount of components.

Another object of the invention is a medicament which contains the above mentioned composition.

In the preferable version of the invention embodiment the medicament has a form of a capsule. In the preferable version of the invention embodiment the medicament contains the composition in amount of 320-490 mg.

FULL DISCLOSURE OF THE INVENTION

One object of the invention is the pharmaceutical composition which contains dry powder of pine (*Pinus*) needles and dry peels and pits of grapes extract and pharmaceutically acceptable additive, dry extracts of *Rhodiola Rosea* (*Rhodiola Rosea*), peony (*Paeonia*), green tea (*Camellia sinensis*), Ginkgo Biloba (*Ginkgo Biloba*), valerian (*Valeriána officinális*) roots, combination of dry powder of pomegranate (Punica granatum) juice and dry extract of pomegranate (Punica granatum) bark and folic acid, in the following ratio of the components in weight % (w %):

| | |
|---|---|
| dry powder of pine needles and dry peels and pits of grapes extract and pharmaceutically acceptable additive | 12-52 |
| dry extract of Rhodiola Rosea | 15-52 |
| dry extract of peony | 18-49 |
| dry extract of green tea | 1.2-5 |
| dry extract of Ginkgo Biloba | 4.5-19 |
| dry extract of valerian roots | 2-14 |
| combination of dry powder of pomegranate juice and dry extract of pomegranate bark | 0.5-7.6 |
| folic acid | 0.1-2 |

As a result of long-term experimental studies, inventors have found that the components in the composition have a synergistic effect, especially, in terms of antidepressant, antiviral and immunomodulatory effects. In addition, the combination of the above components ensures effective removal of heavy metals, including lead, from the body.

The composition is prepared as follows: initially, the components included in the composition are prepared separately. Extract of pine needles and dry peels and pits of grapes is prepared according to the method described in Georgian Patent GE5361 (Vazha Khositashvili, Levan Khositashvili, Babry Oren) 26.12.2011). Liquid pharmaceutically acceptable additive is added to the obtained extract, preferably sucrose. The extract and the pharmaceutically acceptable additive are mixed in the same ratio as described in Georgian Patent GE5361 (4). Finally obtained mixture is dried till making a dry powder. Drying is possible by any method known in the pharmaceutical industry, preferably spray drying is used. Extracts of *Rhodiola Rosea*, peony, green tea, *Ginkgo Biloba*, valerian roots, pomegranate bark are prepared separately. Extracts are prepared by any technology known in the pharmaceutical industry. Obtained liquid extracts are dried separately. Drying is possible by any method known in the pharmaceutical industry, preferably spray drying is used. Finally, dry extracts are obtained. Pomegranate juice is obtained by any known technology, preferably by pressing. Obtained juice is dried. Drying is possible by any method known in the pharmaceutical industry, preferably spray drying is used. Finally, dry powder is obtained, which is mixed with dry extract of already prepared pomegranate bark in order to obtain a combination. The powders obtained separately by the method described above are mixed together (except for the dry extract of pomegranate bark) until a homogeneous mass is obtained. The combination of dry powder of pomegranate juice and dry extract of pomegranate bark is added to the resulting mixture and mixed again until a homogeneous mass is obtained. The components are mixed in such a ratio that the finally obtained composition contains ingredients in the following ratio in w %:

| | |
|---|---|
| dry powder of pine needles and dry peels and pits of grapes extract and pharmaceutically acceptable additive | 12-52 |
| dry extract of Rhodiola Rosea | 15-52 |
| dry extract of peony | 18-49 |
| dry extract of green tea | 1.2-5 |
| dry extract of Ginkgo Biloba | 4.5-19 |
| dry extract of valerian roots | 2-14 |
| combination of dry powder of pomegranate juice and dry extract of pomegranate bark | 0.5-7.6 |
| folic acid | 0.1-2 |

In the preferable version of the invention embodiment the combination of dry powder of pomegranate juice and dry extract of pomegranate bark contains equal amounts of components.

One more object of the invention is a medicament. In preferable version of the embodiment of the invention the medicament has a form of a capsule. In order to obtain the medicament in a form of a capsule, gelatinous capsules (5) are filled with the above mentioned composition, by the method well-known in the pharmaceutical industry. In preferable version of the invention embodiment the capsule contains the composition in amount of 320-480 mg. Indications for using the medicament are as follows: treatment and prophylaxis of depression, impaired immune conditions, bacterial and viral infections, inflammatory conditions, as well as removal of heavy metals, and radionuclides from the body, reducing the amount of free radicals in the body.

Dosage of the medicament (preferably capsule) is 320-480 mg (one capsule) 2-3 times per day. Peroral administration of the medicament is possible, though it is better to dissolve the powder contained in the medicament (for example a capsule) in 32'C pre-boiled (6) water and take it orally in a form of liquid. The medicament is administered 15-30 minutes before eating.

SPECIFIC EXAMPLES OF CARRYING OUT OF THE INVENTION

Example 1

The composition contains the components in the following ratio in mg:

| | |
|---|---|
| dry powder of pine needles and dry peels and pits of grapes extract and pharmaceutically acceptable additive | 120 |
| dry extract of Rhodiola Rosea | 120 |
| dry extract of peony | 80 |
| dry extract of green tea | 10 |
| dry extract of Ginkgo Biloba | 24 |
| dry extract of valerian roots | 24 |

| -continued | |
|---|---|
| combination of dry powder of pomegranate juice and dry extract of pomegranate bark | 20 |
| folic acid | 2 |
| total mass of the composition | 400 mg (7) |

Example 2

The composition contains the components in the following ratio in mg:

| | |
|---|---|
| dry powder of pine needles and dry peels and pits of grapes extract and pharmaceutically acceptable additive | 80 |
| dry extract of Rhodiola Rosea | 80 |
| dry extract of peony | 72 |
| dry extract of green tea | 12 |
| dry extract of Ginkgo Biloba | 28 |
| dry extract of valerian roots | 25 |
| combination of dry powder of pomegranate juice and dry extract of pomegranate bark | 20 |
| folic acid | 3 |
| total mass of the composition | 320 mg |

Example 3

The composition contains the components in the following ratio in mg:

| | |
|---|---|
| dry powder of pine needles and dry peels and pits of grapes extract and pharmaceutically acceptable additive | 161.5 |
| dry extract of Rhodiola Rosea | 161.5 |
| dry extract of peony | 98 |
| dry extract of green tea | 6 |
| dry extract of Ginkgo Biloba | 23 |
| dry extract of valerian roots | 27 |
| combination of dry powder of pomegranate juice and dry extract of pomegranate bark | 10 |
| folic acid | 3 |
| total mass of the composition | 490 mg |

A number of researches have been carried out to study the effectiveness of the composition of the invention.

Study of Antidepressant Effect

1. Study of the Impact on Motivation

Mice with an average weight of 22-30 g were divided into four groups, with 5 mice in each of them. On the first day, all mice were placed in a 200 ml, 8 cm deep tank filled with water at 22° C. (7) The mice were allowed to swim in the tank for 15 minutes. The next day, the first group was given 10% solution of valerian extract at a dose of 10 ml/kg. The second group was given 10% aqueous solution of the composition described in U.S. Ser. No. 11/083,764 at a dose of 10 ml/kg. The third group was given 10% aqueous solution of the composition described in Example 1 at a dose of 10 ml/kg. The fourth group was a control group, which was given physiological saline at a dose of 10 ml/kg. All groups of mice were given the agents orally. In 30 minutes after administration, all groups of mice were placed in the same tanks for 6 minutes. In 2 minutes after they started swimming, the mice were observed and those periods when a mouse moved the limbs were recorded; thus, the total time of swimming was recorded as the time of spontaneous swimming. Increase of spontaneous swimming time means improved motivation. The study data are shown in Table 1, each respective row of which shows the mean spontaneous time value of each group of mice.

TABLE 1

| Group Number | Time of Spontaneous Swimming |
|---|---|
| 1 | 171 ± 27 |
| 2 | 155 ± 28 |
| 3 | 218 ± 12 |
| 4 | 148 ± 21 |

2. Study of the Impact on Behavioral Activity

Mice with an average weight of 22-30 g were divided into four groups, with 5 mice in each of them. The first group was given 10% solution of valerian extract at a dose of 10 ml/kg. The second group was given 10% aqueous solution of the composition described in U.S. Ser. No. 11/083,764 at a dose of 10 ml/kg. The third group was given 10% aqueous solution of the composition described in Example 2 at a dose of 10 ml/kg. The fourth group was a control group, which was given 0.2% agar suspension at a dose of 10 ml/kg. All groups of mice were given the agents orally. In one hour after administration, all groups of mice were injected intraperitoneally with a mixture of 400 μg/kg lipopolysaccharide in 10 mg/kg physiological saline. Then the animals were placed in a light stripe of a box having light and dark fields and their behavior was observed for three minutes. This action was repeated for two hours and the average time of the mice being in the bright field and the average number of field changes were determined. Mice are nocturnal animals, which is why they prefer to be in the dark field. Prolonged stay in the bright field of the mouse and decrease in the frequency of field changes indicate a decrease in the interest of the animal and, consequently, demotivation. The study data are shown in Table 2.

TABLE 2

| Group Number | Time of Being in Light Field (sec) | Number of Field Changes |
|---|---|---|
| 1 | 109 ± 18 | 5.5 ± 1.8 |
| 2 | 129 ± 21 | 4.6 ± 2.8 |
| 3 | 87 ± 9 | 8.1 ± 2.8 |
| 4 | 135 ± 32 | 4.4 ± 2.8 |

3. Study of the Effect on Intracerebral Amines

Mice with an average weight of 22-30 g were divided into four groups, with 5 mice in each of them. The first group was given 10% solution of valerian extract at a dose of 10 ml/kg. The second group was given 10% aqueous solution of the composition described in U.S. Ser. No. 11/083,764 at a dose of 10 ml/kg. The third group was given 10% aqueous solution of the composition described in Example 3 at a dose of 10 ml/kg. The fourth group was a control group, which was given physiological saline at a dose of 10 ml/kg. All groups of mice were given the agents orally. In 60 minutes after administration, brains of the mice were taken and striatum were collected. The striatum was homogenized in physiological saline with the amount which was 10 times more (v/w). After homogenization, hydrochloric acid was added to the solution in order to remove proteins. Using sodium acetate, after lowering the pH of the solution to 3.5, serotonin and norepinephrine concentrations were determined via liquid chromatography. Increase of serotonin and norepinephrine concentrations means improved antidepressant effect. The study data are shown in Table 3, which shows the mean values of serotonin and norepinephrine concentrations of each group of mice.

TABLE 3

| Group Number | Serotonin Concentration (ng/ml) | Norepinephrine Concentration (ng/ml) |
|---|---|---|
| 1 | 0.241 ± 0.021 | 0.501 ± 0.018 |
| 2 | 0.141 ± 0.025 | 0.455 ± 0.031 |
| 3 | 0.294 ± 0.023 | 0.621 ± 0.021 |
| 4 | 0.139 ± 0.023 | 0.453 ± 0.034 |

In Vivo Study of Anti-Inflammatory Effect

BALB/c mice were divided into groups, with 10 mice in each of them. The first group was given aqueous solution of dry powder of pine needles and dry peels and pits of grapes extract and sucrose. (8) with 5 mg/kg dosage of an active ingredient. The second group was given aqueous solution of the composition described in U.S. Ser. No. 11/083,764 with 5 mg/kg dosage of an active ingredient. The third group was given aqueous solution of the composition described in example 1, with 5 mg/kg dosage of an active ingredient. In one hour after administration, all groups were intraperitoneally injected with lipopolysaccharide (LPS), dissolved in sterile, apirogenic saline at a dose of 1 mg/kg. The negative control group was receiving saline solution in a form of intraperitoneal injection. Rolipram (30 mg/kg, orally) (9) was used as a standard pharmaceutical drug. After an hour, blood was drawn from the abdominal artery. Heparin (5 μl) was used as an anticoagulant in tubes filled with the collected blood. Plasma was removed from the blood by centrifugation at room temperature, was divided into aliquots and stored at −70° C. until analysis. TNF-α levels were tested in blood samples by ELISA and the percentage of inhibition of TNF-α release compared to the control group was determined. The obtained results are shown in Table 4.

TABLE 4

| Group Number | Inhibition % |
|---|---|
| 1 | 28.38 ± 7.34 |
| 2 | 93.2 ± 3.65 |
| 3 | 90.4 ± 3.25 |

Study of Antibacterial Effect

Patients suffering from bacterial infection of the oral cavity were divided into 4 groups of three patients. The first group was given aqueous solution of dry powder of pine needles and dry peels and pits of grapes extract and sucrose (320 mg dry powder was dissolved in 150 ml water). The second group was given aqueous solution of the composition described in U.S. Ser. No. 11/083,764 to gargle three times per day (320 mg dry powder was dissolved in 150 ml water). The third group was given aqueous solution of the composition described in example 2, to gargle three times per day (320 mg dry powder was dissolved in 150 ml water). The fourth group was a control one and was given placebo. One hour before starting the treatment and one hour after the last treatment with aqueous solutions the patients were given physiological solution to gargle for 30 sec. After that, 0.5 ml of each gargled physiological solution were cultivated on agar for 36 hours, in lab standard conditions, after this the number of bacteria was counted. The obtained average data are shown in Table 5.

TABLE 5

| Group | Bacterial Count (x10⁵) | |
|---|---|---|
| Number | before treatment | after treatment |
| 1 | 46 | 39.8 |
| 2 | 41.5 | 5.6 |
| 3 | 42 | 6.1 |
| 4 | 43 | 44.5 |

In Vitro Study of Antioxidant Effect

Three samples were examined to evaluate antioxidant effectiveness. The first sample was the aqueous solution of the composition described in Example 1; the second sample was the aqueous solution of the composition described in U.S. Ser. No. 11/083,764; the third sample was the solution of pine needles and dry peels and pits of grapes extract and sucrose (10) (medicine described in Georgian Patent GE5362); the fourth sample was control—Ethylenediaminetetraacetate.

Method: evaluation was done by determining the intermediate product of the lipid oxidation process, malondialdehyde (MDA). Amount of MDA increases under the influence of ferrous sulfate ($FeSO_4$), this moment was used as a model for the activated oxidation process. Sequence of analysis: 0.1 ml of test sample, 1 μmol of ferrous sulfate solution was added to 0.3 ml of blood serum and incubated at 37° C. for 15 min. Then 3 ml of 3% orthophosphoric acid and 1 ml of 0.6% thiobaric acid were added to the incubation mixture. The mixture was placed on a boiling water bath for one hour. Then 4 ml of butanol was added. The obtained mixture was centrifuged for 10 minutes at 3000 rpm. In the obtained supernatant, the optical density (E) was determined on a spectrometer on a wavelength of 535 nm. MDA concentration (C) was determined by the formula $C=E \times 84.5$ μmol/L. The difference between the background concentration of MDA and iron activated was 100%, while the antioxidant activity of the samples was conditionally expressed in %. The obtained results are shown in Table 6.

TABLE 6

| Sample Number | Relative Antioxidant Activity in % |
|---|---|
| 1 | 172 |
| 2 | 176 |
| 3 | 157 |
| 4 | 92 |

In Vivo Study of the Effectiveness of Removing Heavy Metals from the Body

The study was conducted on children with econephropathies who were from regions contaminated with heavy metal salts. The children were given the medicine offered by the invention, namely, a 320 mg capsule three times per day during seven days. Urinary excretion of heavy metals before and during the treatment was investigated to evaluate the effectiveness of the medicine. The results of the study are shown in Table 7.

TABLE 7

| Heavy Metal | Excretion Before Treatment μg/l | Excretion During Treatment μg/l |
|---|---|---|
| Arsenic | 1.1 | 12.0 |
| Chromium | 1.4 | 3.7 |
| Cadmium | 0.01 | 0.02 |
| Lead | 0.1 | 1.7 |

Study of Radio-Protective Effect (11)

White rats (*Rattus*) were used for the study. A model of acute radiation sickness was created with single, total, equal irradiation of animals. The animals were divided into 8 groups with 10 animals in each. Four groups of animals were irradiated at a dose of 8 Gy, which causes death of bone marrow. The remaining four groups of animals were irradiated at a dose of 10 Gy, which causes irreversible damage to the gastrointestinal tract.

Irradiation of animals in the first four groups at a dose of 8 Gy was performed according to the following scheme: Group 1 (control): only irradiation; Group 2: the aqueous solution of the composition described in Example 3, at a dose of 7 mg/kg of an active ingredient, 3 times per day, for 5 days and then irradiation; Group 3: irradiation and then the aqueous solution of the composition described in Example 3, at a dose of 7 mg/kg of an active ingredient, 3 times per day, till the death of an animal or for 15 days; Group 4: the aqueous solution of the composition described in Example 3, at a dose of 7 mg/kg of an active ingredient, 3 times per day, for 5 days, then irradiation and then the aqueous solution of the composition described in Example 3, at a dose of 7 mg/kg of an active ingredient, 3 times per day, till the death of an animal or for 15 days.

Irradiation of animals in the second four groups at a dose of 10 Gy was performed according to the following scheme: Group 5 (control): only irradiation; Group 6: the aqueous solution of the composition described in Example 3, at a dose of 7 mg/kg of an active ingredient, 3 times per day, for 5 days and then irradiation; Group 7: irradiation and then the aqueous solution of the composition described in Example 3, at a dose of 7 mg/kg of an active ingredient, 3 times per day, till the death of an animal or for 15 days; Group 8: the aqueous solution of the composition described in Example 3, at a dose of 7 mg/kg of an active ingredient, 3 times per day, for 5 days, then irradiation and then the aqueous solution of the composition described in Example 3, at a dose of 7 mg/kg of an active ingredient, 3 times per day, till the death of an animal or for 15 days. The average life expectancy of each group of animals and the percentage of survived animals in the group were determined during the experiment. The results of the study are shown in Table 8.

TABLE 8

| Group No | Average Life Expectancy (days) | Number of Survived Animals |
|---|---|---|
| 1 | 10 | 0 |
| 2 | 15 | 1 (10%) |
| 3 | 14 | 1 (10%) |
| 4 | 20 | 2 (20%) |
| 5 | 5 | 0 |
| 6 | 10 | 0 |
| 7 | 8 | 0 |
| 8 | 12 | 1 (10%) |

Study of Immunomodulatory Activity

1. Study of Blast Transformation of Lymphocytes

Research was carried out to study the effect of herbal extracts on cellular immunity. Determination of In vitro blast transformation or blasto-genesis of normal lymphocytes was used to assess the above mentioned. Blasto-genesis is the initial step in the induction of cellular immunity and is associated with the secretion of various interleukins which are essential for intercellular interaction of the immune system.

The study was carried out on three samples. The first sample was the aqueous solution of the composition described in Example 1, at a concentration of 4 mg/ml; the second sample was the aqueous solution of the composition described in U.S. Ser. No. 11/083,764 at a concentration of 4 mg/ml; the third sample was the aqueous solution of dry powder of pine needles and dry peels and pits of grapes extract and sucrose at a concentration of 4 mg/ml.

Blast transformation was measured via a conventional lymphocyte stimulation test wherein $^3$H-thymidine was added to lymphocyte suspension, followed by incubation, cell harvesting and measuring radioactivity of the harvested cells. A high radioactivity count indicates that the lymphocytes have undergone transformation and taken up the $^3$H-thymidine.

The lymphocytes were obtained from the blood of healthy people by separation via density gradient method in Ficoll Isopaque. Multi-well plates were prepared containing lymphocyte suspensions in Hanks solution supplemented with 10% fetal calf serum, penicillin and streptomycin. The first sample was added to the wells of the first plate, 20 μl to each well, the second sample was added to the wells of the second plate, 20 μl to each well and the third sample was added to the wells of the third plate, 20 μl to each well. One more plate was used for control and nothing was added to its wells. The final volume of lymphocyte suspension in each well was 0.2 ml. The plates were then incubated for 72 hours at 37'C in a $CO_2$ incubator. To each well 0.05 ml of $^3$H-thymidine was added after incubation, followed by a further 24 hours of incubation at 37° C. Then the cells were harvested with an automatic harvester, and radioactivity (12) was measured with a scintillation counter. The obtained results are shown in Table 9.

TABLE 9

| Sample | Average Count of $^3$H-thymidine Uptake | Stimulation Index |
|---|---|---|
| Control | 284 counts/min | 0 |
| Sample 1 | 868 counts/min | 3.06 |
| Sample 2 | 895 counts/min | 3.15 |
| Sample 3 | 364 counts/min | 1.28 |

The obtained results show that the composition of the invention significantly increases cellular immunity by stimulating blastogenesis, which finally boosts secretion of cytokines. The mentioned results also show that the composition of the invention in terms of enhancing cellular immunity practically does not differ from the composition described in U.S. Ser. No. 11/083,764, which is a strong immuno-modulator. (13)

2. Study of Stimulation of Cytokine Production

Research was carried out to study the stimulation of cytokines production by herbal extracts. The study was carried out on three samples. The first sample was the aqueous solution of the composition described in Example 1, at a concentration of 10%; the second sample was the aqueous solution of the composition described in U.S. Ser. No. 11/083,764 at a concentration of 10%; the third sample was the aqueous solution of dry powder of pine needles and dry peels and pits of grapes extract and sucrose at a concentration of 10%.

The effect of the samples on cytokine production in peripheral mononuclear blood cells of healthy people, was measured using the method described in the following documents: D. Schols and E. De Clencq, Human Immunodeficiency Virus Type gp120 Induces Anergy In Human Peripheral Blood Lynphocytes By Inducing Interleukin Production, J. Virol., 1996, Vol. 70, p. 4953-4960. The obtained results are shown in Table 10.

TABLE 10

| Sample | IL-2 (pg/ml) | IL-4 (pg/ml) | IL-10 (pg/ml) | IFN-γ (pg/ml) |
|---|---|---|---|---|
| Control | insignificant | not detected | 35 | 31 |
| Sample 1 | 65 | not detected | 681 | 275 |
| Sample 2 | 68 | not detected | 711 | 286 |
| Sample 3 | 27 | not detected | 282 | 112 |

The obtained results demonstrate that the composition of the invention significantly boosts cytokine production in peripheral mononuclear blood cells of people and in this respect it practically does no differ from the composition described in U.S. Ser. No. 11/083,764, which is a strong immunomodulator.

Study on Antiviral Activity

1. In vitro Study of Antiviral Activity Against Herpes Simplex Virus Type 2

The antiviral activity of three samples against the second type of herpes simplex virus was studied. The first sample was the aqueous solution of the composition described in Example 1, at a concentration of 4 mg/ml; the second sample was the aqueous solution of the composition described in U.S. Ser. No. 11/083,764, at a concentration of 4 mg/ml; the third sample was the aqueous solution of pine needles and dry peels and pits of grapes extract and sucrose dry powder, at a concentration of 4 mg/ml.

For the study Vero cells (renal cells from monkey) were used. The cells were cultivated in the $CO_2$-thermostat at 37° C. temperature, on plates with the growth medium of RPMI-1640+ fetal serum (Nuclon, Surface, Denmark). For studying antiviral activity, the one day and night cultures of Vero cells with confluent cell monolayer were used. The growth medium was removed; experimental samples were applied on the cell monolayer. In one hour after the application, the second type of herpes simplex virus (HSV) at a dose of 100 $TCD_{50}$ ($TCD_{50}$ is tissue cytopathogenic dose of the virus, which causes damage to 50% of cell monolayer) was added and then supporting medium was placed into the wells (serum-free nutritive medium).

Cultures were incubated in $CO_2$ thermostat during 3 days, with daily microscopic control and registration of viral reproduction which was expressed by HSV cytopathic effect on Vero cells in comparison with control culture, where the monolayer was not treated with experimental samples.

HSV cytopathic effect is morphologically expressed as formation of symplasts or round cells along with proliferation and creation of giant multinuclear cells.

After three days, cultures were collected from the plate wells and the infectious titers for each experimental sample were determined. HSV reproduction titers are shown in Table 11.

TABLE 11

| Sample   | Infectious Titer 1 g $TCD_{50}$ |
|----------|---------------------------------|
| Sample 1 | 2.0                             |
| Sample 2 | 2.0                             |
| Sample 3 | 5.0                             |
| Control  | 7.0                             |

The results provided in the Table show that the composition of the invention has the ability to dramatically suppress the second type of herpes simplex virus.

2. In Vitro Study of Anti-Influenza Activity

The antiviral activity of three samples against the influenza virus (H1N1) was studied. The first sample was the aqueous solution of the composition described in Example 1, at a concentration of 4 mg/ml; the second sample was the aqueous solution of the composition described in U.S. Ser. No. 11/083,764, at a concentration of 4 mg/ml; the third sample was the aqueous solution of one needles and dry peels and pits of grapes extract and sucrose dry powder, at a concentration of 4 mg/ml.

For the Study MDCK Madin-Darby Canine Kidney (14) cells (renal cells from dog) were used. The cells were cultivated in the $CO_2$ thermostat at 37° C., on plates with the growth medium of RPMI-1640+ fetal serum (Nuclon, Surface, Denmark). For enhance of cell sensitivity to contamination with the influenza virus, the processing with trypsin was performed. For studying antiviral activity, the one day and night cultures of MDCK cells with confluent cell monolayer were used. Growth medium was removed; experimental samples were applied on the cell monolayer. In one hour after the application of the samples, the influenza virus was added and the supporting medium was placed into the wells (serum-free nutritive medium).

Cultures were incubated in Ca-thermostat during 3 days, with daily microscopic control and registration of viral reproduction which was expressed by cytopathic effect of the influenza virus on MDCK cells in comparison with control culture, where the monolayer was not treated with experimental samples.

After three days, cultures were collected from the plate wells and the infectious titers for each experimental sample were determined. Reproduction titers of the influenza virus are shown in Table 12.

TABLE 12

| Sample   | Infectious Titer 1 g $TCD_{50}$ |
|----------|---------------------------------|
| Sample 1 | 2.0                             |
| Sample 2 | 2.0                             |
| Sample 3 | 5.0                             |
| Control  | 6.0                             |

The results provided in the Table show that the composition of the invention has the ability to dramatically suppress the influenza virus.

3. Study of Antiviral Activity Against Herpes Virus

The antiviral activity of three samples against the herpes virus was studied. The first sample was the aqueous solution of the composition described in Example 1, at a concentration of 4 mg/ml; the second sample was the aqueous solution of the composition described in U.S. Ser. No. 11/083,764, at a concentration of 4 mg/ml; the third sample was the aqueous solution of pine needles and dry peels and pits of grapes extract and sucrose dry powder, at a concentration of 4 mg/ml.

During the research as a form of the virus was used the virus isolated from the blood serum of a person with herpetic infection. The virus-containing material was a culture fluid which was taken from the swine embryo kidney cell cultures infected with the virus isolated by the method mentioned above, at the peak of cytopathic manifestation. For the research the virus at a dose of 10 $TCD_{50}$ was used.

The invention claimed is:

1. A medicament composition based on plant raw materials, the composition comprising by weight percent (wt %) thereof:
   (a) 12-52 wt % dry powder of pine needles and dry peels and pits of grapes extract and pharmaceutically acceptable additive;
   (b) 15-52 wt % dry extract of *Rhodiola rosea;*
   (c) 18-49 wt % dry extract of peony;
   (d) 1.2-5 wt % dry extract of green tea;
   (e) 4.5-19 wt % dry extract of *Ginkgo biloba;*
   (f) 2-14 wt % dry extract of valerian roots;
   (g) 0.5-7.6 wt % of a combination of dry powder of pomegranate juice and dry extract of pomegranate bark; and
   (h) 0.1-2 wt % folic acid.

2. The medicament composition of claim 1, wherein the composition comprises equal amounts of the dry powder of pomegranate juice and the dry extract of pomegranate bark.

3. The medicament composition of claim 2, wherein the composition is in the form of a capsule.

4. The medicament composition of claim 3, wherein the capsule comprises the composition in an amount of 320-480 mg.

\* \* \* \* \*